(12) United States Patent
Van Noy

(10) Patent No.: US 9,078,744 B2
(45) Date of Patent: Jul. 14, 2015

(54) SINGLE OPTIC ACCOMMODATIVE INTRAOCULAR LENS SYSTEM

(75) Inventor: Stephen Van Noy, Southlake, TX (US)

(73) Assignee: NOVARTIS AG, Basel (CH)

( * ) Notice: Subject to any disclaimer, the term of this patent is extended or adjusted under 35 U.S.C. 154(b) by 491 days.

(21) Appl. No.: 12/699,279

(22) Filed: Feb. 3, 2010

(65) Prior Publication Data
US 2010/0204788 A1 Aug. 12, 2010

Related U.S. Application Data

(60) Provisional application No. 61/151,552, filed on Feb. 11, 2009.

(51) Int. Cl.
*A61F 2/16* (2006.01)

(52) U.S. Cl.
CPC ............ *A61F 2/1613* (2013.01); *A61F 2/1629* (2013.01); *A61F 2/1648* (2013.01); *A61F 2/1694* (2013.01)

(58) Field of Classification Search
CPC ............................ A61F 2/1613–2/1632; A61F 2/1648–2002/1651; A61F 2002/1681; A61F 2220/0025; A61F 2220/0033; A61F 2220/0091; A61F 2250/0008; A61F 2250/0065
USPC ............. 623/6.37, 6.43, 6.4, 6.41, 6.34, 6.32, 623/6.38
See application file for complete search history.

(56) References Cited

U.S. PATENT DOCUMENTS

| | | | | |
|---|---|---|---|---|
| 4,124,905 A | * | 11/1978 | Clark | 623/6.12 |
| 4,629,462 A | | 12/1986 | Feaster | |
| 5,716,403 A | * | 2/1998 | Tran et al. | 623/6.46 |
| 5,824,074 A | * | 10/1998 | Koch | 623/6.34 |
| 6,013,101 A | * | 1/2000 | Israel | 623/6.43 |
| 6,197,059 B1 | * | 3/2001 | Cumming | 623/6.39 |
| 6,302,911 B1 | * | 10/2001 | Hanna | 623/6.39 |
| 6,761,737 B2 | * | 7/2004 | Zadno-Azizi et al. | 623/6.37 |
| 6,972,033 B2 | * | 12/2005 | McNicholas | 623/6.37 |
| 2002/0103490 A1 | | 8/2002 | Brady | |
| 2002/0138140 A1 | * | 9/2002 | Hanna | 623/6.37 |
| 2003/0114927 A1 | * | 6/2003 | Nagamoto | 623/6.37 |
| 2003/0204255 A1 | * | 10/2003 | Peng et al. | 623/6.34 |
| 2004/0006387 A1 | * | 1/2004 | Kelman | 623/6.36 |
| 2004/0039446 A1 | * | 2/2004 | McNicholas | 623/6.37 |
| 2004/0162612 A1 | * | 8/2004 | Portney et al. | 623/6.34 |
| 2004/0236422 A1 | * | 11/2004 | Zhang et al. | 623/6.34 |
| 2006/0047339 A1 | * | 3/2006 | Brown | 623/6.13 |
| 2006/0235515 A1 | | 10/2006 | Chassain | |
| 2007/0016293 A1 | * | 1/2007 | Tran | 623/6.34 |
| 2007/0106381 A1 | | 5/2007 | Blake | |

(Continued)

*Primary Examiner* — Paul Prebilic
(74) *Attorney, Agent, or Firm* — Jason Finch

(57) ABSTRACT

A single-optic accommodative lens system includes two intraocular elements designed to be located within the capsular bag to extend depth of focus and/or restore accommodation following cataract extraction of a natural lens. A first intraocular element comprises a circumferential capsular ring having interlock features to couple to and control the dynamic vault response of a second intraocular element. This second intraocular element comprises an intraocular lens (IOL) having an optic and a plurality of haptics and is designed to move axially in response to changes in the geometry of the eye capsule and thus provide a range of accommodative power. The IOL further comprises interlock features complementary to the interlock features of the first intraocular element for coupling the IOL to the capsular ring in a manner that provides for controlled movement of the IOL in response to capsular forces.

21 Claims, 4 Drawing Sheets

(56) References Cited

U.S. PATENT DOCUMENTS

| | | | |
|---|---|---|---|
| 2007/0260308 A1* | 11/2007 | Tran | 623/6.34 |
| 2009/0018652 A1* | 1/2009 | Hermans et al. | 623/6.38 |
| 2010/0204787 A1* | 8/2010 | Noy | 623/6.34 |
| 2012/0010704 A1* | 1/2012 | Bumbalough | 623/6.39 |
| 2012/0078363 A1* | 3/2012 | Lu | 623/6.37 |

* cited by examiner

SINGLE OPTIC ACCOMMODATIVE INTRAOCULAR LENS SYSTEM

This application claims priority to U.S. Provisional Application Ser. No. 61/151,552 which was filed on Feb. 11, 2009.

This invention relates generally to the field of intraocular lenses (IOLs) and, more particularly, to accommodative IOLs.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In the way, the natural lens can be focus alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Typically, when a cataract or other disease requires the removal of the natural lens and replacement with an artificial IOL, the IOL is a monofocal lens, requiring that the patient use a pair of spectacles or contact lenses for near vision. Advanced Medical Optics has been selling a bifocal IOL, the Array lens, for several years, but this lens has not been widely accepted. The Bausch and Lomb Crystalens™ accommodative IOL is also available, but has a number of disadvantages.

Several other designs for accommodative IOLs are being studied. For example, see U.S. Pat. Nos. 6,197,059, 5,674, 282, 5,496,366 and 5,476,514 (Cumming), the entire contents of which being incorporated herein by reference. The lens described in these patents is a single optic lens having flexible haptics that allow the optic to move forward and backward in reaction to movement of the ciliary muscle. Similar designs are described in U.S. Pat. No. 6,302,911 B1 (Hanna), 6,261, 321 B1 and 6,241,777 B1 (both to Kellan), the entire contents of which being incorporated herein by reference. The amount of movement of the optic in these single-lens systems, however, may be insufficient to allow for a useful range of accommodation. In addition, as described in U.S. Pat. Nos. 6,197, 059, 5,674,282, 5,496,366 and 5,476,514, the eye must be paralyzed for one to two weeks in order for capsular fibrosis to entrap the lens that thereby provide for a rigid association between the lens and the capsular bag. In addition, the commercial models of these lenses are made from a hydrogel or silicone material. Such materials are not resistive to the formation of posterior capsule opacification ("PCO"). The treatment for PCO is a capsulotomy using a Nd:YAG laser that vaporizes a portion of the posterior capsule. Such destruction of the posterior capsule may destroy the mechanism of accommodation of these lenses.

Prior art accommodative lenses also lack extended depth of focus in addition to having poor accommodation performance. Prior art lenses further require precise lens sizing for proper function over a range of capsular bag sizes and lack long term capsular fixation and stability. Lastly, as current lens replacement surgeries move towards smaller incision size, IOLs in general require the ability to be delivered through such small incisions.

Therefore, a need continues to exist for a safe and stable accommodative intraocular lens system that provides accommodation over a broad and useful range.

BRIEF SUMMARY OF THE INVENTION

Embodiments of the present invention improve upon the prior art by providing a single-optic accommodative lens system comprising two intraocular elements. The two intraocular elements are designed to be located within the capsular bag to extend depth of focus and/or restore accommodation following extraction of a natural lens. A first intraocular element comprises a circumferential capsular ring having interlock features to couple to and control the dynamic vault response of a second intraocular element. This second intraocular element comprises an intraocular lens (IOL) having an optic and a plurality of haptics and is designed to move axially in response to changes in the geometry of the eye capsule and thus provide a range of accommodative power. The IOL further can comprise interlock features complementary to the interlock features of the first intraocular element for coupling the IOL to the capsular ring in a manner that provides for controlled movement of the IOL in response to capsular forces. Capsular force can be applied to the IOL from anterior, posterior and/or intermediate sections of the capsule equator, resulting in movement of the IOL and commensurate accommodation.

When implanted in the capsular bag, the capsular ring provides a platform for axially and rotationally positioning the IOL within the capsular bag that can provide for precise positioning of a toric or custom IOL. The embodiments of the accommodative lens system of the present invention can provide a continuous barrier to lens epithelial cell proliferation to help reduce anterior and posterior capsular opacification (ACO, PCO). Embodiments of the accommodative lens system have a lens design selected to provide between about 0.25 and about 5 diopters of depth of focus and/or refractive accommodation as a function of displacement in response to changes in capsular bag tension related to ciliary muscle movement during accommodation.

The IOL optic can be a monofocal or multifocal optical element having a positive or negative power. The capsular ring can be located anteriorly or posteriorly within the capsular bag. The IOL haptics are relatively firm, yet still flexible and can be configured to interlock with features of the capsular ring. This interlocking feature of the two lenses ensures stable relative fixation of the IOL optic. The capsular ring and related interlocking features can also be designed to permit secondary implantation with existing monofocal IOLs.

Accordingly, one objective of the present invention is to provide a safe and biocompatible intraocular lens.

Another objective of the present invention is to provide a safe and biocompatible intraocular lens that is easily implanted in the posterior chamber.

Still another objective of the present invention is to provide a safe and biocompatible intraocular lens that is stable in the posterior chamber.

Still another objective of the present invention is to provide a safe and biocompatible accommodative lens system.

These and other advantages and objectives of the present invention will become apparent from the detailed description and claims that follow.

DETAILED DESCRIPTION OF THE INVENTION

Figure 1A:
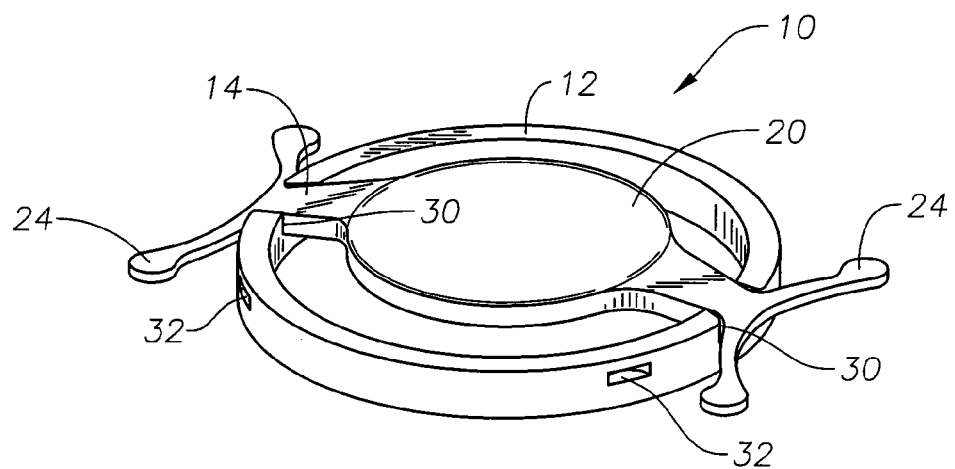
FIG. 1A is an enlarged view of an assembled embodiment of the lens system of the present invention in a relaxed state showing exemplary notched ring and IOL components, in this embodiment a notched anterior ring surface and a four-point fixated IOL positioned toward an anterior capsular surface, and showing haptic recesses in the ring for haptic nesting upon compression.
Figure 1B:
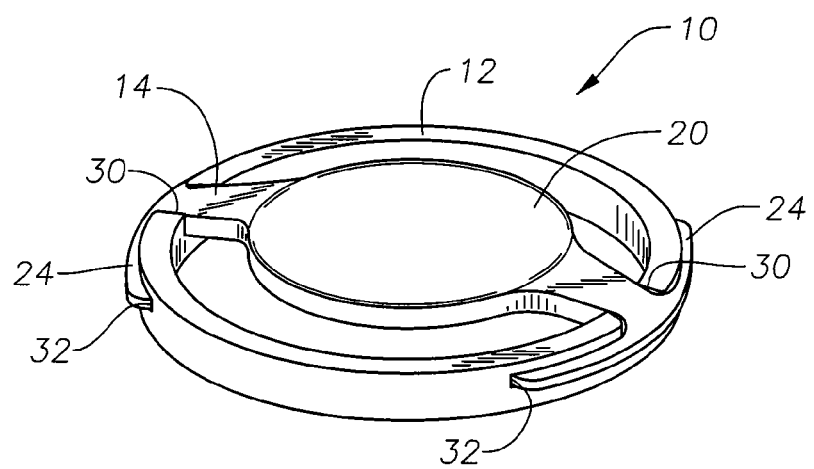
FIG. 1B is an enlarged view of the assembled embodiment of the lens system of the present invention shown in FIG. 1A with the four-point fixated IOL positioned toward the anterior capsular surface in a compressed state.
Figure 2A:
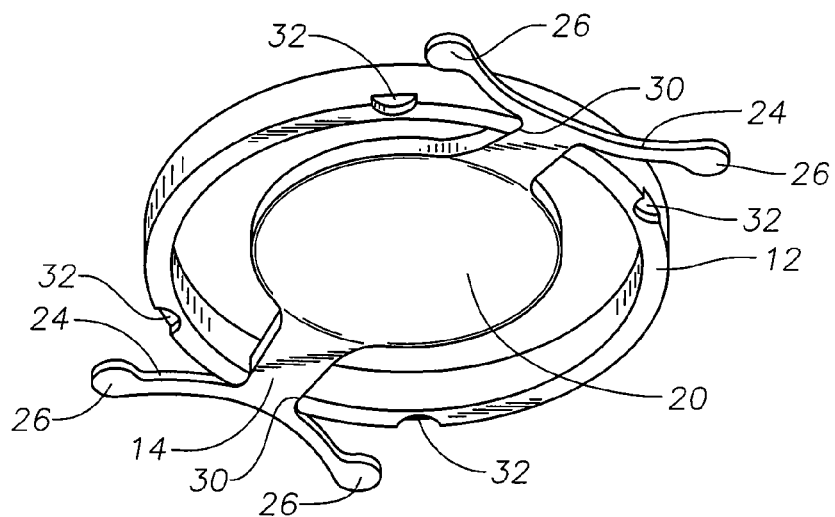
FIG. 2A is an enlarged view of an assembled embodiment of the lens system of the present invention in a relaxed state showing exemplary notched ring and IOL components, in this embodiment a notched posterior ring surface and a four-point fixated IOL positioned toward the anterior capsular surface.
Figure 2B:
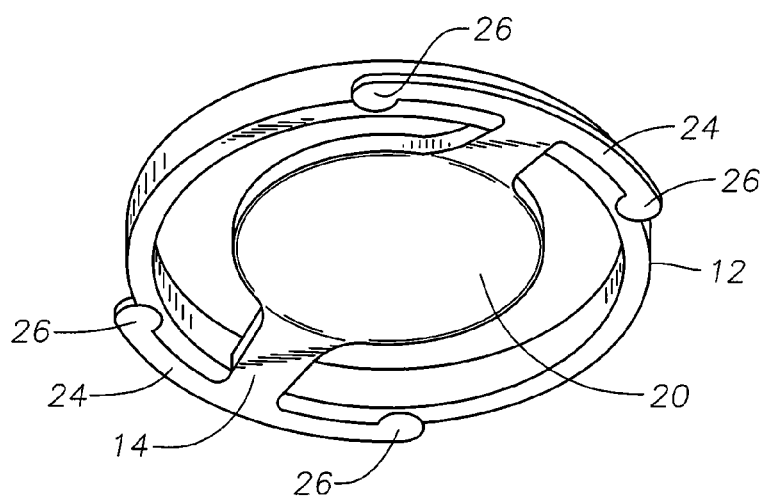
FIG. 2B is an enlarged view of the assembled embodiment of the lens system of the present invention shown in FIG. 2A with the four-point fixated IOL positioned toward the anterior capsular surface in a compressed state.
Figure 3A:
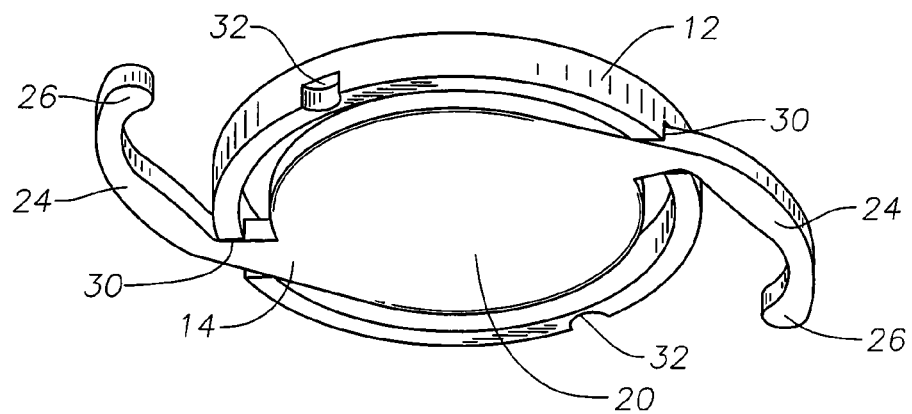
FIG. 3A is an enlarged view of an assembled embodiment of the lens system of the present invention in a relaxed state showing exemplary notched ring and IOL components, in this embodiment a notched posterior ring surface and a single-piece two-point fixated IOL positioned toward the posterior capsular surface.
Figure 3B:
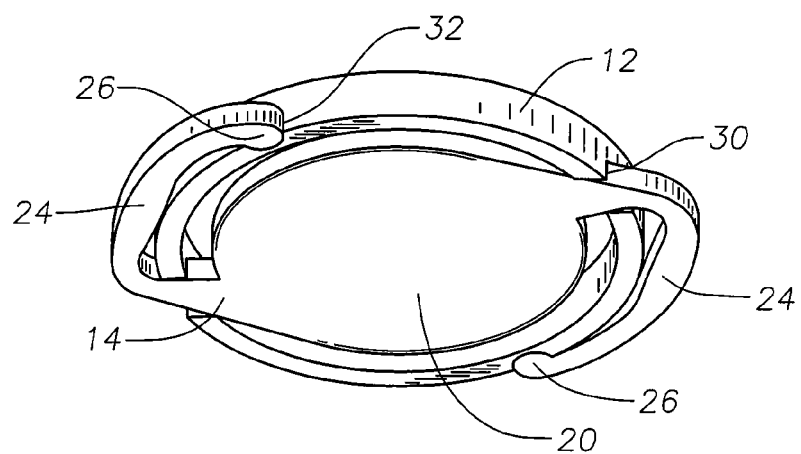
FIG. 3B is an enlarged view of the assembled embodiment of the lens system of the present invention shown in FIG. 3A with the single-piece IOL positioned toward the posterior capsular surface in a compressed state.

As best seen in the FIG.S, lens system 10 of the present invention generally consists of capsular ring 12 and IOL 14. IOL 14 comprises an optic 20 and a plurality of haptics 24. Ring 12 and IOL 14 are preferably made from a soft, foldable material that is resistive to the formation of PCO, such as a soft acrylic, or a hydrogel or silicone. Optic 20 can be a monofocal or multifocal optical element having any suitable negative or positive power. Ring 12 can be located posteriorly or anteriorly to IOL 14. Haptics 24 can be used to size the lens system 10 over a range of capsular bag sizes. IOL 14 (optic 20) can move along the optical axis of an eye in which it is implanted in response to dynamic capsular forces resulting from movement of the ciliary muscle.

Capsular ring 12 further comprises interlock features designed to couple capsular ring 12 to IOL 14. These features can comprise notches 30 in the circular outermost surface (anterior surface) of capsular ring 12 as shown in FIGS. 1A-1B, 4A, and 5A-5B, notches 30 in the posterior surface of capsular ring 12 as shown in FIGS. 2A-3B, through-holes (not shown) in the wads of ring 12 through which a haptic 24 can pass, or a combination of the three interlock features. Other interlock features, as may be apparent to those having skill in the art, can also be used to couple capsular ring 12 and IOL 14. Capsular ring 12 can be located anteriorly or posteriorly within the capsular bag. Capsular ring 12 can thus couple to IOL 14 and control the axial displacement of IOL 14. Those having skill in the art will recognize that the materials of ring 12 and IOL 14 will help determine the extent of control over the movement of the components of lens system 10. When coupled, IOL 14 and ring 12 present a continuous lens/ring surface to the anterior/posterior capsule with minimal space for LEC passage. The interlock features of the ring 12 and IOL 14 help to correctly position and control the axial position of IOL 14 and capsular tension to maximize the accommodative lens system response. In some embodiments, capsular ring 12 can be used as a drug delivery device in ways that will be known to those having skill in the art.

IOL 14 haptics 24 are relatively firm, yet still flexible so as to allow some, but not excessive, flexing in response to ciliary muscle contraction and relaxation and can be configured to couple with the interlock features of ring 12 to couple ring 12 and IOL 14. The complementary interlocking features of ring 12 and IOL 14 help ensure stable relative fixation of the optic 20. Because capsular ring 12 provides capsular support, IOL 14 can be thinner in cross-section than would be possible without ring 12, and still provide optical performance comparable to a thicker IOL. The interlock features help ensure that IOL 14 remains stable during capsular contractions and permits a thinner optic 20.

The embodiments of the lens system 10 of the present invention are designed to be located within the capsular bag to extend depth of focus and/or restore accommodation following extraction of the natural lens. The capsular ring and IOL system and related interlocking features is designed to present a continuous barrier to lens epithelial cell ("LEC") proliferation to minimize PCO. IOL 14 optic power can be selected to provide between about 0.25 and about 5 diopters of depth of focus and/or refractive accommodation as a function of displacement in response to changes in capsular bag tension related to ciliary muscle movement during accommodation. Capsular ring 12 and related interlocking features can also be designed to permit secondary implantation with existing monofocal IOLs.

Interlock features of ring 12 (notch, hole, or other attachment feature) enable the embodiments of the present invention to couple ring 12 and IOL 14 together such that they present a continuous lens/ring surface to the anterior or posterior capsule with minimal space for lens epithelial cell passage. Ring 12 and IOL 14 can be temporarily or permanently joined before or after lens delivery into the eye (implantation). Optic 20 of IOL 14 of the embodiments of the present invention can incorporate specialized monofocal, multifocal or varifocal optics including spherical, astigmatism, higher-order, chromatic, combined, refractive surgery induced, and custom aberration correcting designs using refractive and/or diffractive technologies including apodization.

Figure 4A:
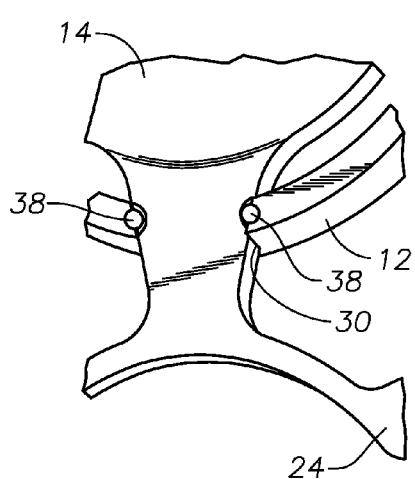
FIGS. 4A and 4B show an enlarged view of one embodiment of the interlocking features of the lens system of the present invention, in this embodiment a ball-detent interlock.
Figure 4B:
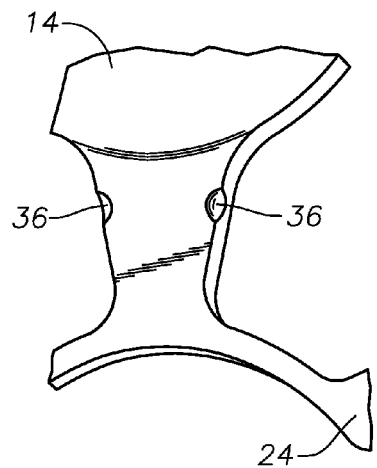
Figure 5A:
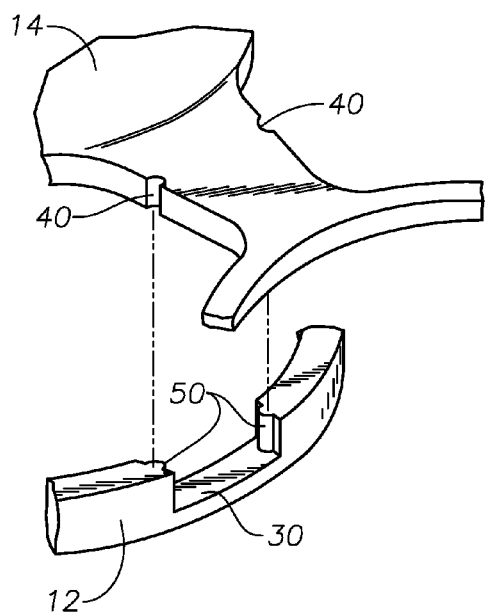
FIGS. 5A and 5B show an enlarged view of another embodiment of the interlocking features of the lens system of the present invention, in this embodiment a tongue-in-groove interlock.
Figure 5B:
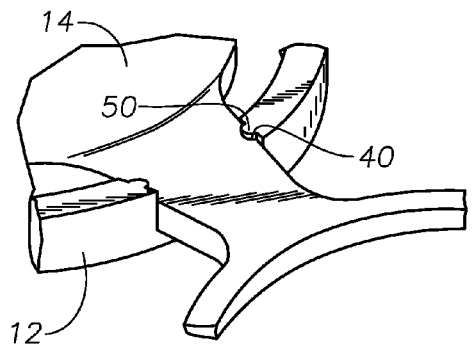

IOL 14 comprises complimentary interlock features to couple with the interlock features of ring 12. Exemplary complimentary interlock features are shown in FIGS. 1-5B and particularly in FIGS. 4A-5B. For example, ring 12 can comprise recesses 32 for nesting of the end pads 26 of haptics 24 when haptics 24 are compressed. Haptic end pads 26 fit into recesses 32. In some embodiments, notches 30 of ring 12 can comprise overlaps 38 extending beyond the inner walls of notches 30 such that they overlap haptics 24 when the ring 12 and IOL 14 are coupled together (a ball-detent interlock). As shown in FIGS. 4A and 4B, overlaps 38 can fit into haptic recesses 36 of IOL 14 haptic 24 and help to securely hold the ring 12 and IOL 14 together. In other embodiments, as shown in FIGS. 5A and 5B, notches 30 can comprise protrusions 50 dimensioned to fit into complimentary grooves 40 (a tongue and groove interlock) on the IOL 14 haptics 24 to couple the ring 12 and IOL 14 together.

Because ring 12 provides capsular support, optic 20 can be thinner and still provide optical performance comparable to a thicker optic. The interlock features help ensure that the optic remains stable during capsular contractions and permit a thinner optic element. Further, because the IOL 14 haptics 24 can extend beyond the outer diameter of ring 12, this helps prevent sub-luxation into the vitreous humor. Embodiments of the lens system 10 of the present invention thus provide an interlocking ring and IOL combination to help ensure stable positioning and control of the IOL 14 in response to dynamic capsular forces. Relative sizing of the IOL 14 overall length and the ring 12 diameter and thickness are important to control the accommodative amplitude of lens system 10. To assist ring 12 in reducing PCO, components of the embodiments of lens system 10 of the present invention can incorporate chemicals, materials and/or specialized features to control PCO or treat ocular diseases, as will be known to those having skill in the art.

In use, IOL 14 and capsular ring 12 can be implanted separately. For example, ring 12 can be implanted into the capsular bag prior to the implantation of IOL 14. IOL 14 can then be implanted and ring 12 and IOL 14 coupled by means of the interlock features discussed above. The sequence of implantation and coupling together of ring 12 and IOL 14 can vary, as will be known to those having skill in the art and as discussed above.

Embodiments of the lens system of the present invention can thus provide for permanent or temporary attachment of supporting ring 12 and IOL 14, permitting the coupled elements to leverage relative movement of the optic 20 into increased depth of focus over a single element system. Embodiments of the lens system of the present invention further incorporate interlock features, different from the prior art, especially in a way that minimizes lens profile to permit insertion of the intraocular elements through a small incision. Utilizing a notch or through-hole interlock feature permits incorporation of an optic 20 while maintaining uninterrupted contact of the lens system 10 with the posterior capsule. The embodiments of this invention can permit relative movement of the IOL 14 and ring 12 to achieve accommodation. It is anticipated that the majority of accommodative action will be driven from one segment of the capsule periphery in response to zonular movement. By selecting anterior, posterior or intermediate haptic positioning, the accommodative performance of the lens system 10 can be maximized.

Haptics 24 help "take-up" slack in the capsular bag which helps address sizing concerns related to accommodating performance and PCO. In addition, the use of a capsular ring 12 provides additional optic stability and added safety against vitreous sub-luxation in the event of intended or Is unintended disruption of posterior capsule integrity. Embodiments of the present invention can incorporate keying of advanced (toric) optics relative to each other to maintain a desired orientation. Further, embodiments of the interlock features of the present invention can be incorporated into embodiments of the invention disclosed in related U.S. Provisional Patent Application, Ser. No. 61/151,381 and filed on Feb. 10, 2009, entitled "Accommodative Intraocular Lens System", the contents of which are fully incorporated by reference herein.

This description is given for purposes of illustration and explanation. It will be apparent to those skilled in the relevant art that changes and modifications may be made to the invention described above without departing from its scope or spirit.

I claim:

1. An intraocular lens system, comprising:
   a) a capsular ring defining an opening there through, the capsular ring having a circular outermost surface with one or more notches therein and one or more interlock features within each of the notches; and
   b) an IOL having an optic and a plurality of haptics, each of the haptics configured to fit within a corresponding one of the notches and comprising one or more haptic recesses corresponding to the one or more interlock features of the corresponding one of the notches, the haptic recesses configured to engage the one or more interlock features to couple to the capsular ring to the IOL, wherein:
   the haptics are dimensioned to fill the notches to present a continuous surface to the anterior or posterior capsule with minimal space for lens epithelial cell passage; and
   the haptics extend outwardly through the notches beyond an outermost surface of the capsular ring when coupled to the capsular ring.

2. The lens system of claim 1, wherein the capsular ring and the IOL comprise a soft acrylic material.

3. The lens system of claim 1, wherein at least one of the capsular ring and the IOL comprise a hydrogel material or a silicone material.

4. The lens system of claim 1, wherein when the IOL and capsular ring are implanted and coupled in an eye, the interlock features distribute forces applied to the haptics of the IOL so that the IOL responds to changes in the geometry of the eye capsule by moving axially to provide a range of accommodation.

5. The lens system of claim 4, wherein the range of accommodation is between about 0.25 diopters and about 5 diopters.

6. The lens system of claim 1, wherein the IOL and capsular ring couple to form a continuous barrier to lens epithelial cell proliferation.

7. The lens system of claim 1, wherein the IOL is a monofocal IOL.

8. The lens system of claim 1, wherein the IOL is a multifocal IOL.

9. The lens system of claim 1, wherein the IOL is a four point fixated IOL.

10. The lens system of claim 1, wherein the IOL is a two-point fixated IOL.

11. The lens system of claim 1, wherein the interlock features comprise a ball-detent interlock.

12. The lens system of claim 1, wherein the interlock features comprise a tongue and groove interlock.

13. The lens system of claim 1, wherein the IOL is a varifocal optic.

14. An accommodative intraocular lens system, comprising:
   a) a capsular ring defining an opening there through, the capsular ring having a circular outermost surface with one or more notches therein and one or more interlock features within each of the notches; and
   b) an IOL having an optic and a plurality of haptics, each of the haptics configured to fit within a corresponding one of the notches and comprising one or more haptic recesses corresponding to the one or more interlock features of the corresponding one of the notches, the haptic recesses configured to engage the one or more interlock features to couple to the capsular ring to the IOL, wherein:
      the haptics are dimensioned to fill the notches to present a continuous surface to the anterior or posterior capsule with minimal space for lens epithelial cell passage;
      the haptics extend outwardly through the notches beyond an outermost surface of the capsular ring when coupled to the capsular ring; and
      when the IOL and capsular ring are coupled and implanted in an eye, the interlock features distribute forces applied to the haptics of the IOL so that the IOL responds to changes in the geometry of the eye capsule by moving axially to provide a range of accommodation.

15. The accommodative lens system of claim 14, wherein the capsular ring and the IOL comprise a soft acrylic material.

16. The accommodative lens system of claim 14, wherein at least one of the capsular ring and the IOL comprise a hydrogel material or a silicone material.

17. The accommodative lens system of claim 14, wherein the range of accommodation is between about 0.25 diopters and about 5 diopters.

18. The accommodative lens system of claim 14, wherein the IOL and capsular ring couple to form a continuous barrier to lens epithelial cell proliferation.

19. The accommodative lens system of claim 14, wherein the IOL is a multifocal IOL.

20. The accommodative lens system of claim 14, wherein the interlock features comprise a ball-detent interlock.

21. The accommodative lens system of claim 14, wherein the interlock features comprise a tongue and groove interlock.

* * * * *